United States Patent
Pusch (10) Patent No.: US 10,478,121 B2
(45) Date of Patent: Nov. 19, 2019

(54) DEVICE AND METHOD FOR DETERMINING AN INCORRECT POSITIONING IN THE ALIGNMENT OF PROSTHESES

(71) Applicant: OTTO BOCK HEALTHCARE GMBH, Duderstadt (DE)

(72) Inventor: Martin Pusch, Duderstadt (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 204 days.

(21) Appl. No.: 14/401,400

(22) PCT Filed: May 14, 2013

(86) PCT No.: PCT/EP2013/001404
§ 371 (c)(1),
(2) Date: Nov. 14, 2014

(87) PCT Pub. No.: WO2013/170945
PCT Pub. Date: Nov. 21, 2013

(65) Prior Publication Data
US 2015/0133821 A1    May 14, 2015

(30) Foreign Application Priority Data
May 14, 2012    (DE) .................. 10 2012 009 507

(51) Int. Cl.
*A61B 5/00* (2006.01)
*A61B 5/11* (2006.01)

(52) U.S. Cl.
CPC ............ *A61B 5/4851* (2013.01); *A61B 5/112* (2013.01); *A61B 5/1121* (2013.01);
(Continued)

(58) Field of Classification Search
CPC ...... A61B 5/4851; A61B 5/112; A61B 5/1121; A61B 5/1122; A61B 5/4585; A61F 2/64; A61F 2/66
See application file for complete search history.

(56) References Cited

U.S. PATENT DOCUMENTS

| 4,488,441 A | 12/1984 | Ramming |
| 4,640,138 A | 2/1987 | Meyer et al. |

(Continued)

FOREIGN PATENT DOCUMENTS

| CA | 2650582 C | 11/2007 |
| DE | 3701372 A1 | 7/1988 |

(Continued)

OTHER PUBLICATIONS

Hong-Liu, Yu, Zhao Sheng-Nan, and Xu Zhao-Hong. "Study on the usability evaluation of prosthetic leg products based on ergonomics." Journal of the Brazilian Society of Mechanical Sciences and Engineering 33.3 (2011): 366-372.*

(Continued)

*Primary Examiner* — Max F Hindenburg
(74) *Attorney, Agent, or Firm* — Holland & Hart, LLP (57) ABSTRACT

A method and a device for determining an incorrect positioning in the alignment of prostheses for the lower extremities are disclosed. The method includes determining inertial measurement data and/or variables derived therefrom using at least one inertial sensor, over at least one walking cycle, for an extremity provided with a prosthesis. The method also includes comparing the inertial measurement data that has been determined and/or the variables derived therefrom with desired values and/or with measurement data that has been determined or variables derived therefrom for the corresponding extremity that is not provided with the prosthesis.

19 Claims, 4 Drawing Sheets

(52) U.S. Cl.
CPC .......... *A61B 5/1122* (2013.01); *A61B 5/4571* (2013.01); *A61B 5/4585* (2013.01); *A61B 5/742* (2013.01); *A61B 5/7405* (2013.01); *A61B 5/746* (2013.01)

(56) References Cited

U.S. PATENT DOCUMENTS

| | | | |
|---|---|---|---|
| 4,849,730 | A | 7/1989 | Izumi et al. |
| 5,490,427 | A | 2/1996 | Yee et al. |
| 5,609,162 | A | 3/1997 | Blumentritt et al. |
| 6,105,438 | A | 8/2000 | Gieseke |
| 6,269,702 | B1 | 8/2001 | Lambson |
| 6,774,885 | B1 * | 8/2004 | Even-Zohar .......... A61B 5/1036 345/156 |
| 6,918,308 | B2 | 7/2005 | Biedermann et al. |
| 7,500,407 | B2 | 3/2009 | Boiten |
| 7,922,774 | B2 | 4/2011 | Macomber et al. |
| 2004/0039454 | A1 * | 2/2004 | Herr .......... A61F 2/64 623/39 |
| 2006/0174718 | A1 | 8/2006 | Morimoto |
| 2008/0276725 | A1 | 11/2008 | Pusch |
| 2008/0285805 | A1 | 11/2008 | Luinge et al. |
| 2008/0288086 | A1 * | 11/2008 | Auberger .......... A61F 2/76 623/27 |
| 2010/0131113 | A1 * | 5/2010 | Even-Zohar .......... A61F 2/68 700/279 |
| 2012/0083901 | A1 * | 4/2012 | Langlois .......... A61F 2/68 623/24 |

FOREIGN PATENT DOCUMENTS

| | | |
|---|---|---|
| DE | 4412377 A1 | 10/1995 |
| DE | 4401036 C2 | 4/2000 |
| DE | 10013059 A1 | 9/2001 |
| DE | 10139333 A1 | 3/2003 |
| DE | 102005051646 A1 | 5/2007 |
| DE | 60131377 T2 | 9/2008 |
| EP | 0575634 A1 | 12/1993 |
| EP | 1559384 A1 | 8/2005 |
| WO | 0172245 A2 | 10/2001 |
| WO | 2004111592 A1 | 12/2004 |
| WO | 2009114909 A1 | 9/2009 |
| WO | WO 2009114909 A1 * | 9/2009 .......... A61B 5/112 |
| WO | 2010120402 A1 | 10/2010 |
| WO | 2012050908 A2 | 4/2012 |

OTHER PUBLICATIONS

Garofalo, Pietro. Development of motion analysis protocols based on inertial sensors. Diss. PhD thesis, University of Bologna, 2010. pp. 1-304.*

Andres, R.O., et al., "Prosthetic alignment effects on gait symmetry: a case study," Clinical Biomechanics 1990, vol. 5, No. 2, pp. 88-96.

PCT International Search Report for PCT International Patent Application No. PCT/EP2013/001404, dated Oct. 24, 2013.

* cited by examiner

DEVICE AND METHOD FOR DETERMINING AN INCORRECT POSITIONING IN THE ALIGNMENT OF PROSTHESES

TECHNICAL FIELD

The invention relates to a method for determining incorrect positions in the alignment of prostheses of the lower extremities and a device for performing such a method.

BACKGROUND

In general, prostheses serve to replace the form and, in particular, the function of limbs which are not present or no longer present. While prostheses made for purely cosmetic reasons do not have to achieve functional objects, prostheses on the lower and upper extremities regularly assume complex problems. Hand prostheses reproduce the function of a natural hand to a large extent, wherein the control of the motor-driven drives in particular requires much outlay.

Prostheses of the lower extremities regularly consist of prosthetic feet, a lower leg tube and optionally a prosthetic knee joint, and are often connected to the remaining stump via sockets. The construction of prostheses of the lower extremities is oriented to the requirements and capabilities of the patients and ranges from a one-axis locking knee joint to computer-controlled prostheses which, on the basis of sensor values, modify the damping properties and engage or switch off drives.

An important aspect in the treatment with prosthetics lies in the correct fitting of the prosthesis to the prosthesis user and the correct assignment of the individual prosthesis components to one another. This alignment of the prosthesis components with respect to one another and to the patient is referred to as the prosthesis alignment or the alignment of the prosthesis in orthopedic technology. Here, the fit and, optionally, the optimization of the settings of upper or below-knee prostheses within the scope of the treatment process is carried out individually for a patient by an orthopedic technician. Here, the orthopedic technician is guided by the alignment instructions and his observations or the impressions of the patient.

In order to assess the alignment, an orthopedic technician can resort to a display system, described in DE 44 01 036 C2, for statistical analysis purposes. The display system provides for a measurement plate and a projection apparatus for visualizing a perpendicular measurement line on the body of a person standing on the measurement plate, wherein the measurement plate is equipped with pressure sensors connected to one another by a circuit, by means of which pressure sensors a drive is controlled, said drive displacing an optical system in a plane parallel to the measurement plate in such a way that a light beam shows the current center of gravity of the person.

US 2008/0285805 A1 has disclosed a system for tracking movements of the human body, in which the movements of the extremities are recorded by 3D inertial angle sensors and wirelessly transferred to an evaluation unit.

WO 2010/120402 A1 relates to a control system for controlling an assigned device with an inertial measurement unit for establishing the orientation of three axes, comprising a computer unit for evaluating the sensor data. The sensor module is connected to the associated apparatus by means of a communication unit and can be controlled thereby. No conclusions about a prosthesis alignment emerge therefrom.

SUMMARY

It is an object of the present invention to provide a method and a device by means of which it is possible, in a simple manner, to be able to assess the prosthesis alignment using gait-analytical measurement data such that, after an appropriate correction, an improved prosthesis alignment can be provided for the patient.

According to the invention, this object is achieved by a method and a device having the features disclosed herein. Advantageous embodiments and developments of the invention are also disclosed.

The method for determining incorrect positions in the alignment of prostheses of the lower extremities provides for inertial measurement data and/or variables derived therefrom, of a treated extremity to be established by means of at least one inertial sensor over at least one gait cycle. A treated extremity is an extremity to which a prosthesis apparatus has been fitted or which has been replaced by a prosthesis apparatus. In the case of transtibial prostheses, the typical components are a prosthetic foot and a below-knee socket, and optionally a pylon, to which the prosthetic foot is attached; in the case of transfemoral prostheses, a thigh socket is provided for holding a thigh stump, a prosthetic knee joint, a lower leg tube and a prosthetic foot. After, for example, the absolute angle, the accelerations, angular rates or yaw rates of an extremity have been measured, for example on the lower leg tube, the lower leg socket or on the thigh socket, and after, optionally, variables such as velocity, movement direction and the orientation of the components in space and in relation to one another, and the movement thereof in space and in relation to one another have been determined or calculated, the established inertial measurement data and/or variables derived therefrom are compared with intended values and/or with established measurement data or derived variables for the corresponding untreated extremity. The intended values can be stored in a storage medium and be based on empirical values or values which were recorded on the patient to be treated.

Here, the established inertial measurement data, e.g. angular values, accelerations, orientations or directions, may relate to variables in different planes. By way of example, angles can be established and compared in the sagittal plane in order to determine how long the step length is, how far the lower leg, and hence the knee, is flexed inward on impact or how far the lower leg swings backward during the swing phase. As an alternative to the comparison of the established measurement data and/or derived variables on the treated extremity with stored intended values, it is possible to establish corresponding measurement data and/or derived variables at the corresponding positions of the untreated, i.e. healthy extremity, e.g. measure absolute angles by means of inertial angle sensors or accelerations by means of accelerometers and base the comparison thereon. By way of example, if a deviating orientation of the thigh, of the lower leg or of the knee angle relative to the contralateral side is established over a gait cycle, the assumption can be made that no harmonic gait pattern is present, wherein the modifications to be undertaken can then be deduced on the basis of the deviations. Depending on the deviation, it will be necessary to realign the individual prosthesis components in relation to one another and on the prosthesis user, for the purposes of which the establishment of the inertial measurement data and/or the variables derived therefrom and the comparison with intended values and/or measurement values or variables derived therefrom of corresponding extremities provides valuable information.

In addition to the absolute angle, inertial sensors also measure the linear accelerations of the respective component, which occur along the axes of a reference system, and also the angular rates or angular velocities around the respective axes in order to be able to derive the rotational movements therefrom.

One embodiment of the invention provides for, in particular, absolute angle sensors to be used as inertial sensors, by means of which the absolute angles of the respective component or extremity are established. This establishment can be effected directly by the sensors, and so there is no need to undertake a conversion, as is required for establishing the derived variable.

The respective inertial measurement value, e.g. the acceleration or the absolute angle, can be established both on the extremity treated with the prosthesis and on the untreated corresponding extremity, wherein measurement values and variables derived therefrom, e.g. the thigh angle, the movement direction, acceleration or acceleration direction, can also be established on the thigh in the case of a transtibial treatment. Fastening to the untreated extremity is required for direct comparison between the extremities.

A development of the invention provides for the knee angle to be determined from the measured absolute angles of the lower leg and of the thigh and compared to intended values and/or the established knee angle of the untreated leg over the respective gait cycle or a mean value of a plurality of gait cycles. The start of a gait cycle can be established on the basis of the characteristic angle profile when walking in a plane, for example on the basis of the knee angle profile. As a result, it is possible to dispense with additional sensors which, for example, measure forces or torques. Therefore, it is possible, on the basis of a pure angle measurement of extremities after applying the prosthesis, to determine as a result of gait-dynamic measurements whether a prosthesis alignment corresponds to the sought-after result, in particular whether a harmonic gait pattern is made possible for a patient, without it being necessary, in the process, to resort to observation of the motion cycle by an orthopedic technician only. Rather, it is possible to draw conclusions as to whether the prosthesis alignment is correct on the basis of objective measurement values, and so it is possible to display angle profiles over a gait cycle and to compare these with a physiological intended curve or with the corresponding angle profile of the untreated leg.

A development of the invention provides for a deviation message to be output in the case of deviations between the established inertial measurement data or the variables derived therefrom and the stored intended values and/or measurement data or variables derived therefrom of the corresponding untreated extremity. As an alternative to a deviation message, a confirmation message can also be output in the case where values are within the intended values and/or within an admissible range of variation around an intended value or around established measurement data or variables derived therefrom for the corresponding untreated extremity such that the orthopedic technician, just like the patient, obtains feedback as to whether or not the static prosthesis alignment is correct.

In addition to the inertial measurement data, e.g. the absolute angles of the lower extremity, that is to say of the foot, of the lower leg and of the thigh, provision is made for a pelvic angle to be established within the frontal plane by at least one inertial angle sensor and for a deviation message to be output if a limit value is exceeded. Tilting of the pelvic angle within the frontal plane during walking is an indication for the Trendelenburg gait. If the pelvic tilt exceeds a defined angle within the frontal plane during walking, this serves as indication for the orthopedic technician that there must be a further adduction of the socket.

Expediently, the inertial measurement data, in particular the absolute angles, are established over a plurality of gait cycles, for example on a treadmill or in a gait analysis apparatus, in order to obtain a database which is as broad as possible for assessing the static alignment of the prosthesis, for optimizing the prosthesis alignment, the setting of the prosthesis, the component selection and the documentation. In addition to establishing the inertial measurement data over a plurality of gait cycles, it is also possible to determine and use the variables derived therefrom over a plurality of gait cycles. It is also possible to better inform and instruct the patient on the basis of the measurement values or the variables derived therefrom, and so an improved acceptance by the patient and an improved use of the prosthesis can be achieved as a result of an improved understanding of the relationships between alignment and behavior of the prosthesis during use.

By means of the inertial angle determination, it is also possible to determine whether the external rotation angle of the knee joint has been set correctly. If a rotation vibration of the treated lower leg is determined during the swing phase, this is an indication for the knee axis not being aligned orthogonally to the movement direction of the thigh, and so the lower leg experiences dynamic imbalance. This dynamic imbalance can be effected by the step identification and the temporal assignment of the measurement values within the gait phase; this is because if a high vibration frequency of the bent lower leg is measured during the swing phase this is an indication for an inappropriate alignment of the joint axis.

The device according to the invention for performing the method as claimed in one of the preceding claims, comprising at least one inertial sensor provides for the latter to be arranged on a component of a prosthesis of the lower extremity and coupled to a comparator, in which the established inertial measurement data, e.g. angle, acceleration, direction, are compared to intended values and/or comparison values, wherein the intended values are stored in the comparator or an appropriate database is connected to the comparator. The comparison values relate to values of the untreated leg of the patient, which are likewise stored in the comparator or made accessible to the latter in a database. By way of example, for making this accessible, a wireless connection can be used.

In order to establish the comparison values on the untreated extremity, provision is made for at least one inertial sensor to be fastened to the untreated extremity in order to establish comparison values. If a plurality of initial sensors are provided on the treated extremity, for example on the lower leg and on the thigh, it is advantageous if corresponding sensors are arranged at corresponding points on the untreated extremity. These sensors are then also connected to the comparator, for example by wires or a radio link.

The output apparatus for the established and, optionally, compared values or for a deviation message if the values for the treated side do not correspond to the intended values or comparison values is likewise connected to the comparator and may be embodied as an acoustic or optical output apparatus. As a result, while walking and while the measurement data is being measured, it is possible for direct feedback to be available, both for the user and the orthopedic technician, as to whether a harmonic gait pattern is present, as to whether the dynamic angle profiles correspond to the prescriptions or intended values, as to whether other measurement data and/or derived variables correspond to the prescriptions or the comparison values and whether or not the prosthesis alignment is set appropriately.

BRIEF DESCRIPTION OF THE DRAWINGS

In the following, the invention will be explained in more detail on the basis of the figures. In detail.

DETAILED DESCRIPTION

Figure 1:
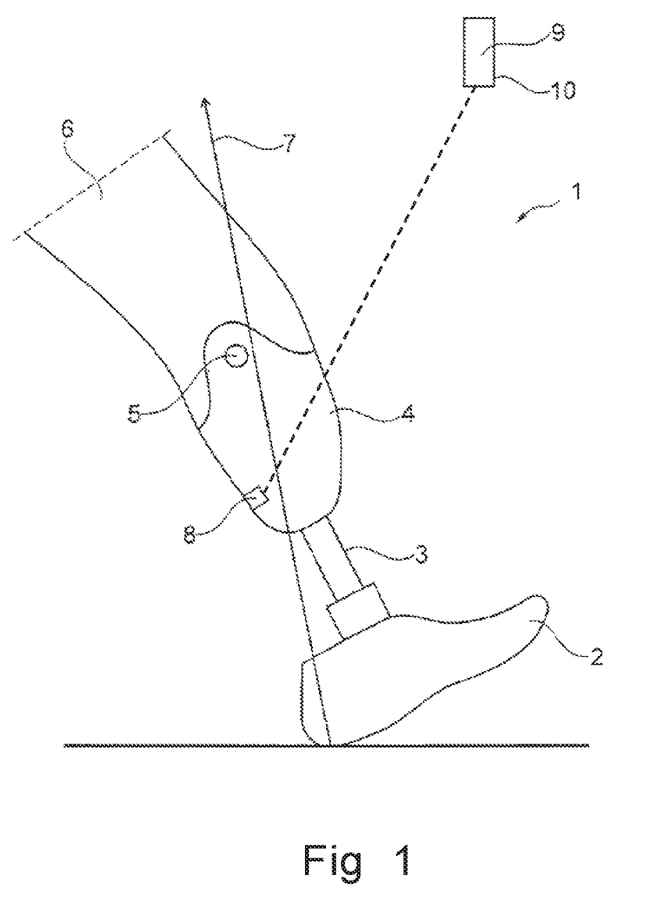
FIG. 1 shows a schematic illustration of a prosthesis with a foot set too far in the anterior direction.

FIG. 1 shows a prosthesis 1 with a prosthetic foot 2, a lower leg tube 3 attached proximally thereto and a socket 4 which establishes a connection to the remaining lower extremity 6. The socket 4 protrudes beyond the still remaining knee joint, and so a knee rotation axis 5 is partly covered. The depicted exemplary embodiment depicts a transtibial prosthesis which does not have a prosthetic knee joint. In principle, the following explanations also apply to transfemoral prostheses with a prosthetic knee joint.

The prosthetic foot 2 is arranged displaceably relative to the lower leg socket 3, for example by means of a displacement adapter or by means of a slot guide (not depicted here), such that, in addition to a rotation around the longitudinal extent of the lower leg tube 3, there can also be a displacement of the prosthetic foot 2 in the anterior direction in the movement direction or in the posterior direction against the movement direction. An inertial sensor 8 in the form of an inertial angle sensor is arranged or worked into the socket 4, by means of which inertial angle sensor the absolute angle of the prosthesis, in the present case of the socket 4 and of the lower leg tube 3, can be established relative to the vertical. Angle sensors which establish the absolute angle relative to the gravitational direction are, in particular, provided as inertial sensors; provision can likewise be made for accelerometers and/or angular rate sensors for recording the inertial measurement data.

By applying further inertial sensors, for example on the thigh and on the hips, it is possible to measure certain body segment angles and/or accelerations in a dynamic fashion. In the case of the angles, these are, in particular, the orientation of the thigh, the orientation of the lower leg, the orientation of the hip and the flexion of the knee from the difference angle between the thigh angle and the lower leg angle in the sagittal plane. A step identification, which admits a temporal assignment of the measured angle values to the respective gait phase, can be realized on the basis of these measured or calculated angles. Therefore, it is possible to achieve a time-resolved angle registration for the standing phase and the swing phase during walking. As a result, it is possible to depict the angle profiles of the respective body segments over a gait cycle, or else over a plurality of gait cycles, and to compare these angle profiles to those of a predetermined intended curve or to values measured at the contralateral, untreated leg. It is also possible to measure the linear accelerations which occur along the axes of a reference system, just as it is possible to measure the angular rates or angular velocities around the respective axes in order to be able to derive the rotational movements therefrom.

A critical parameter when fitting transtibial prostheses lies in sufficient knee flexion and sufficient knee extension after the heel strike. This parameter can be substantially influenced by the positioning of the prosthetic foot 2 relative to the lower leg tube 3 and therefore relative to the socket 4. A change in the positioning of the prosthetic foot 2 in the anterior/posterior direction leads to a change in the profile of the floor reaction force 7 during striking, heel-toe walking and at the end of the standing phase during toe off. This change in the profile results in a change in the effective knee torque around the knee axis 5 which has a stretching or flexing effect depending on the position of the floor reaction forces 7 relative to the joint axis 5.

In FIG. 1, the prosthetic foot 2 is displaced maximally in the anterior direction such that, in the case of the heel strike at the beginning of the standing phase, the vector of the floor reaction force 7 is arranged anteriorly to the knee rotation axis 5. This leads to a stretching torque around the knee rotation axis, and so no knee flexion, or only little knee flexion, can be established during the heel strike. If the patient exhibits no knee flexion while walking in a straight line in the plane after the heel strike, but rather there is detection of stretching and, accompanying this due to the non-existent deflection, a pelvic tilt in the frontal plane after the heel strike, an orthopedic technician can deduce that the prosthetic foot 2 is arranged too far in the anterior direction, and so an adjustment in the posterior direction is required. This setting can be brought about iteratively until the desired knee angle is achieved during normal walking.

Figure 2:
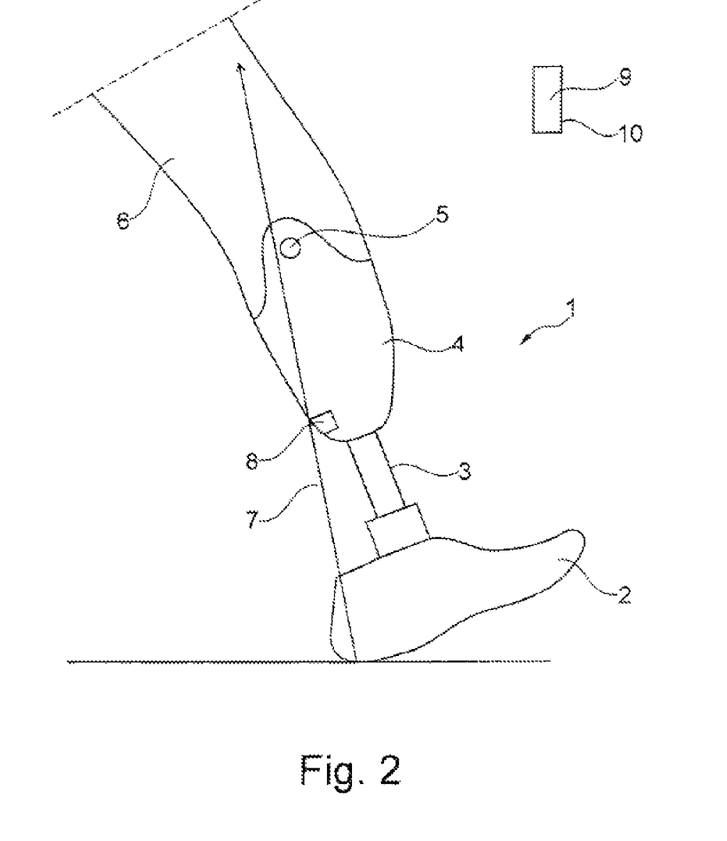
FIG. 2 shows a heel strike with a foot too far in the posterior direction.

FIG. 2 shows the maximum position of the prosthetic foot 2 in the posterior direction; in the case of a heel strike, the vector of the floor reaction force 7 extends behind the knee rotation axis 5, and so there is very strong flexion due to the inflected knee torque. This unwanted knee flexion must be absorbed by the patient using the treated leg, which is disadvantageous. Therefore, the orthopedic technician will analyze the angle profile after the heel strike and will determine that there is a knee flexion which is too strong or too quick, and hence there is a displacement of the socket 4 relative to the vertical which is too quick. This leads to the prosthetic foot 2 having to be displaced further in the anterior direction until the patient starts to flex the knee in a controlled manner.

Determining the alignment by means of the heel strike is made simpler if the knee angle is available as a measurement value, and so additional inertial angle sensors 8 would have to be arranged on the thigh. The knee angle is calculated by forming the difference between the segment angles from the thigh and lower leg in the sagittal plane. A recommendation in respect of the direction in which the prosthetic foot needs to be displaced can now be provided on the basis of the measured knee angle curve or, optionally, also on the basis of only the measured lower leg curve for a plurality of steps. This recommendation can be brought about by means of an output apparatus 10 on a comparator 9, which is connected to the sensor 8 or the sensors 8. The measured angles are processed within the comparator 9 and the output command or output value is established, optionally on the basis of intended curves or measured angle values of the contralateral, untreated leg.

Figure 3:
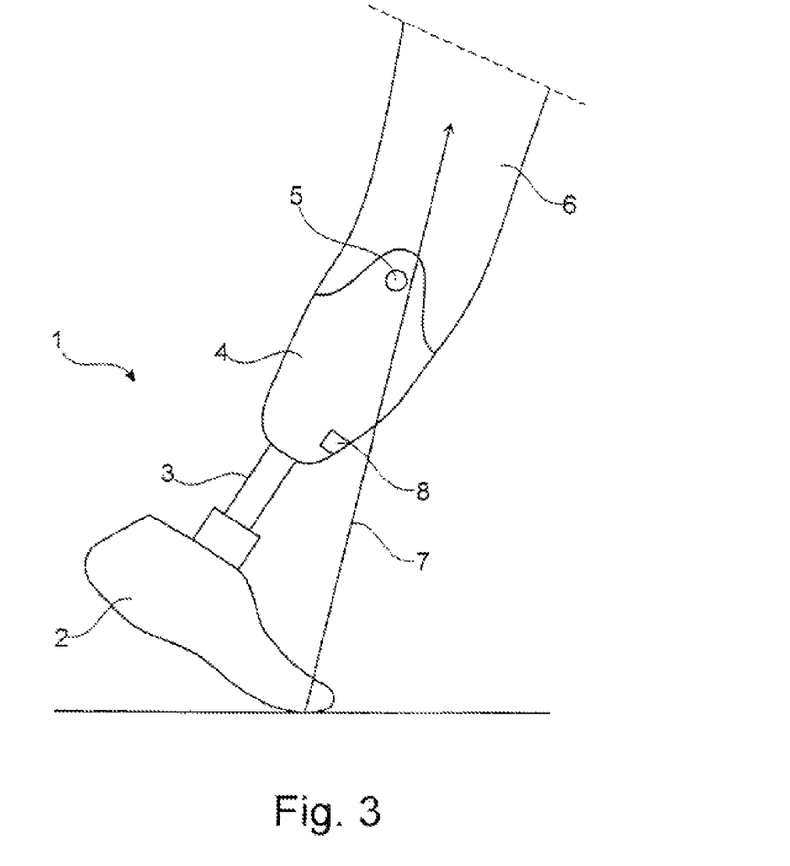
FIG. 3 shows a toe off with a foot too far in the anterior direction.
Figure 4:
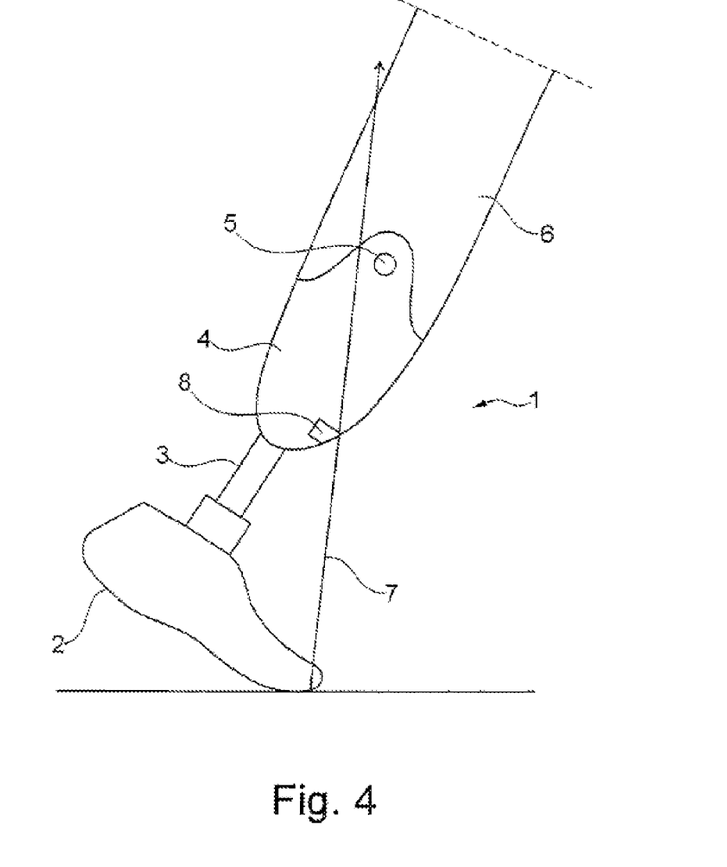
FIG. 4 shows a toe off with a foot too far in the posterior direction.

A further indication as to whether or not the prosthesis alignment is appropriate can be effected during the toe-off phase, the so-called "toe off", which is depicted in FIGS. 3 and 4. In the case of an orientation of the prosthetic foot 2 which is too far in the anterior direction in accordance with FIG. 3, a knee-extending torque is exerted anteriorly of the knee rotation axis 5 due to the profile of the resulting floor reaction force 7, and so inward flexion after the toe off is not possible, or only possible with difficulties. Accordingly, it is necessary to position the prosthetic foot 2 further in the posterior direction.

If the prosthetic foot 2 is too far in the posterior direction, as shown in FIG. 4, the resulting floor reaction force vector 7 extends posteriorly of the knee rotation axis 5 during the toe off, which leads to a sudden and uncontrolled inward flexion or to an increased load on the patient in the case of a transtibial prosthesis. If no knee flexion or no sufficiently large increase in the initial angle of the socket 4 and of the thigh is determined during the toe off, or just thereafter, the assumption can be made that the positioning is too far in the anterior direction, while in the case of a quick angle enlargement and a very far swing-through and a sudden inward flexion, the assumption can be made that the positioning is too far in the posterior direction, and so an appropriate adjustment becomes necessary in order to compensate for this. On the basis of the established values, a signal as to whether the alignment corresponds to the prescriptions or whether changes, and which changes, need to be undertaken, i.e. whether there should be a displacement in the anterior or posterior direction, is output by means of the output apparatus 10.

A physiologically correct gait is, inter alia, characterized in that the segment angles of thigh and lower leg of both legs describe an almost identical motion cycle and scope of movement during normal walking in a plane. If, in the case of a prosthesis wearer, the prosthesis-side thigh angle has a reduced scope of movement in the sagittal plane, this can be an indication for a flexion contracture not considered during the prosthesis alignment. Thus, if the scope of movement of the right and of the left thigh of the patient is measured directly during walking by means of inertial sensors, it is possible to establish different scopes of movement due to the deviating inertial angle during a gait cycle or during a step. To the extent that it is the prosthesis-side scope of movement that is less, an indication in respect of a flexion contracture being present is output by means of the comparator 9 and the output apparatus 10, and so the prosthesis alignment must be modified accordingly.

Arranging an inertial angle sensor 10 in such a way that a pelvic tilt in the frontal plane can be established during walking can, if the predetermined angle is exceeded, optimize the prosthesis alignment by a further adduction of the socket 4.

If the lower leg tube 3 or the socket 4 of the treated side experiences a rotational vibration during the swing phase, this is an indication for an incorrectly set external rotation angle of the knee rotation axis 5. This means that, in the case of transfemoral prostheses, the knee rotation axis 5 does not extend orthogonally to the movement direction of the thigh such that the lower leg experiences a dynamic imbalance. If an imbalance is measured due to the high vibration frequency of the flexed lower leg, this is an indication for an incorrect alignment of the knee rotation axis 5, and so a corresponding correction of the alignment must be undertaken.

In the case of transtibial prostheses, a sufficient flexion of the knee joint may be present if the knee flexion present is greater than 5°, if the knee angular velocity is less than 100°/s and the extension of the knee in the standing phase is greater than half of the knee flexing angle. If a sufficient flexion is not determined in the knee joint, the prosthetic foot 2 should be positioned iteratively in the anterior direction until an easily controllable movement of the knee occurs. The determination in respect of the approximately physiological knee angle can be effected by an acoustic signal by means of the output apparatus 10; in the case of measurement values outside of determined parameters or away from the symmetry values of the contralateral leg, a negatively sounding signal may be emitted or an optical warning apparatus may be activated.

In the case of transfemoral prostheses, it may be the case that a hip flexion contracture becomes more noticeable when walking than it was in the patient history. In order to establish this, the thigh angle movement when walking is measured on the prosthesis side and contralaterally in the sagittal plane. In the case of a smaller movement on the prosthesis side, for example less than 70% of the angular values for the contralateral side, the socket flexion within the prosthesis is increased until the extent of movement is harmonized.

A further problem of transfemoral prostheses may lie in the fact that the capability of the gluteus medius is weaker than determined in the patient history. The external rotation of the knee axis is then less than what is actually required for the individual style of the gait. In order in this case to determine errors in the prosthesis alignment, the pelvic angle is measured while walking. If a tilt of the hip for positioning the body's center of gravity over the prosthesis, or if a sinking of the hip on the contralateral side, is measured, for example as more than 5° in relation to the horizontal, the abduction angle is increased incrementally until the patient no longer departs from a pelvic tilt in the range of ±5° when walking.

An inertial angle measurement on the lower leg is likewise performed in order to rotate the socket 4 about the longitudinal axis thereof or in order to rotate the pendulum motion of the lower leg in the frontal plane. If an angle movement of e.g. greater than 5° is measured during walking in the plane, the knee axis 5 is incrementally rotated outwardly until the angular movement remains in a tolerable range.

The invention claimed is:

1. A method for determining positions for alignment of a prosthetic foot relative to a lower leg tube as part of an alignment of a lower extremity device, comprising:
    establishing, using sensor data measured by at least one inertial sensor connected to the lower extremity device, over at least one gait cycle for a treated extremity, at least one of inertial measurement data and variables derived from the inertial measurement data for the treated extremity, the inertial measurement data comprising absolute angles of a lower leg and a thigh of the treated extremity;
    determining a knee angle of the lower leg and the thigh from the absolute angles of the lower leg and thigh;
    comparing the inertial measurement data and the knee angle with intended values;
    determining positions for alignment of the prosthetic foot relative to the lower leg tube based on the comparing.

2. The method as claimed in claim 1, further comprising establishing at least one of inertial measurement data and variables derived from the inertial measurement data for an untreated extremity.

3. The method as claimed in claim 1, further comprising outputting a deviation message when an established angle deviates from the at least one of intended values, established measurement data, and derived variables for the untreated extremity, or outputting a confirmation message when the established angle is within the at least one of intended values, established measurement data, and derived variables for the untreated extremity.

4. The method as claimed in claim 1, further comprising establishing a pelvic angle in a frontal plane using the at least one inertial angle sensor, and outputting an error message if the pelvic angle exceeds a limit value.

5. The method as claimed in claim 1, wherein the inertial measurement data is established over a plurality of gait cycles.

6. A device for determining positions for alignment of a prosthetic foot relative to a lower leg tube as part of an alignment of a lower extremity prosthesis, the device comprising:
a lower extremity prosthesis having a component;
at least one inertial sensor arranged on the component, the at least one inertial sensor measuring inertial measurement data, the inertial measurement data comprising absolute angles of a lower leg and a thigh of the treated extremity, the absolute angles of the lower leg and thigh being used to determine a knee angle;
a comparator coupled to the at least one inertial sensor, the comparator being configured to compare the inertial measurement data and the knee angle to intended values, the comparison being used to determining positions for alignment of the prosthetic foot relative to the lower leg tube.

7. The device as claimed in claim 6, further comprising at least one additional inertial sensor configured to be arranged on an untreated extremity, the at least one additional inertial sensor connected to the comparator.

8. A method for determining positions for alignment of a prosthetic foot relative to a lower leg tube as part of an alignment of a lower extremity device that is operable on a treated extremity of a user, the method comprising:
providing at least one inertial sensor and a lower extremity device;
determining inertial measurement data and variables for the treated extremity using the at least one inertial sensor over at least one gait cycle during use of the lower extremity device, the variables including a knee angle;
comparing the inertial measurement data and the variables with intended values;
determining positions for alignment of the prosthetic foot relative to the lower leg tube based on the comparing.

9. The method as claimed in claim 8, further comprising:
measuring absolute angles as the inertial measurement data, the absolute angles being used to determine the knee angle.

10. The method as claimed in claim 8, further comprising:
establishing at least one of inertial measurement data and variables derived from the inertial measurement data on an untreated extremity.

11. The method as claimed in claim 8, wherein the lower extremity device comprises a lower leg and a thigh, the lower leg and the thigh each having absolute angles, the method further comprising:
determining the knee angle from the absolute angles of the lower leg and of the thigh;
comparing the knee angle to intended knee angle values.

12. The method as claimed in claim 8, further comprising:
establishing an angle of the lower extremity device;
outputting a deviation message when the angle of the lower extremity device deviates from the intended values, or outputting a confirmation message when the established angle is within the intended values.

13. The method as claimed in claim 8, further comprising:
establishing a pelvic angle in a frontal plane by using the at least one inertial angle sensor;
outputting an error message if the pelvic angle exceeds a limit value.

14. The method as claimed in claim 8, further comprising:
establishing the inertial measurement data over a plurality of gait cycles.

15. The method as claimed in claim 1, wherein the lower extremity device is a prosthesis.

16. The method as claimed in claim 8, wherein the lower extremity device is a prosthesis.

17. The method as claimed in claim 1, further comprising:
providing a recommendation for adjustment of the lower extremity device based on the comparison of the knee angle with the intended values; and
adjusting an alignment setting of the lower extremity device based on the recommendation.

18. The method of claim 1, wherein the inertial measurement data further comprises at least one of linear accelerations of the lower extremity device and angular rates or angular velocities of the lower extremity.

19. The device as claimed in claim 6, further comprising an acoustic or optical output device in electronic communication with the comparator, the acoustic or optical output device being configured to output at least one of the intended values and a deviation message, and to output at least one recommendation for adjustment of an alignment setting of the lower extremity device based on the comparison performed by the comparator.

* * * * *